(12) United States Patent
Vorberg et al.

(10) Patent No.: US 7,314,965 B2
(45) Date of Patent: Jan. 1, 2008

(54) CATALYSTS CONTAINING COPPER AND ZINC FOR THE PURIFICATION OF ETHYLENE

(75) Inventors: Gerald Vorberg, Speyer (DE); Wolfgang Jürgen Pöpel, Darmstadt (DE); Ernest Miesen, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 770 days.

(21) Appl. No.: 10/477,356

(22) PCT Filed: May 17, 2002

(86) PCT No.: PCT/EP02/05470

§ 371 (c)(1),
(2), (4) Date: Nov. 12, 2003

(87) PCT Pub. No.: WO02/094435

PCT Pub. Date: Nov. 28, 2002

(65) Prior Publication Data

US 2004/0176653 A1    Sep. 9, 2004

(30) Foreign Application Priority Data

May 21, 2001    (DE) ................ 101 24 962

(51) Int. Cl.
*C07C 7/148*  (2006.01)
*C07C 7/00*   (2006.01)
*C07C 7/10*   (2006.01)
*B01J 23/06*  (2006.01)
*B01J 23/72*  (2006.01)

(52) U.S. Cl. ............. 585/845; 585/809; 585/833; 502/343; 502/345

(58) Field of Classification Search ............ 585/809, 585/833, 853, 854, 845; 502/343, 345
See application file for complete search history.

(56) References Cited

U.S. PATENT DOCUMENTS

| 3,549,719 A |   | 12/1970 | Duyverman et al. |
|---|---|---|---|
| 4,593,148 A |   | 6/1986 | Johnson et al. |
| 4,871,710 A |   | 10/1989 | Denny et al. |
| 5,229,346 A |   | 7/1993 | Mori et al. |
| 5,453,412 A | * | 9/1995 | Deckers et al. ............ 502/342 |
| 5,767,039 A | * | 6/1998 | Yamagishi et al. ......... 502/342 |
| 6,054,497 A | * | 4/2000 | Sofianos et al. ............ 518/713 |
| 6,124,234 A |   | 9/2000 | Fetzer et al. |
| 6,689,713 B1 | * | 2/2004 | Zhao et al. ................ 502/345 |

FOREIGN PATENT DOCUMENTS

| DE | 43 01 469 | 7/1974 |
|---|---|---|
| WO | 02/70653 | 9/2001 |
| WO | 02/47818 | 6/2002 |

OTHER PUBLICATIONS

Ind.Org.Chem.,Weissermel, 1976, 57-59, 65 and 66.
Ziegler-Natta-Catalysts and Polymerisation, Boor, 1979 pp. 1, 2, 280-285.
Petrochemical Tech.Quarterly, 103-107, 1997.

* cited by examiner

*Primary Examiner*—Glenn Caldarola
*Assistant Examiner*—In Suk Bullock
(74) *Attorney, Agent, or Firm*—Novak Druce & Quigg, LLP

(57) ABSTRACT

Catalysts for the purification of ethylene containing copper and zinc, optionally one or more promoters or supports. These catalysts are produced by precipitation, drying, calcination and compression, optionally with the addition of additives, the compressed catalyst particles are calcinated at a temperature between from 300 to 700° C.

10 Claims, No Drawings

CATALYSTS CONTAINING COPPER AND ZINC FOR THE PURIFICATION OF ETHYLENE

The present invention relates to catalysts for the purification of ethylene comprising copper and zinc and, if desired, one or more promoters and supports and produced by precipitation, drying, calcination and pressing, with or without addition of additives, wherein the pressed catalyst particles are subjected to further calcination at from 300 to 700° C.

Ethylene is an important raw material for the production of polyethylene. The industrial-scale preparation of ethylene, e.g. by cracking of naphtha in a steam cracker, gives impure ethylene from which catalyst poisons which adversely affect the performance of polymerization catalysts such as organoaluminum Ziegler-Natta catalysts or chromium-containing Phillips catalysts have to be removed (Industrielle organische Chemie, K. WeiBermel and H.-J. Arpe, Verlag Chemie, 1976, pages 57, 58, 59, 65, 66, and Ziegler-Natta Catalysts and Polymerisations, J. Boor, Academic Press 1979, pages 1, 2, 280 to 285).

Petrochemical Technology Quarterly (PTQ), pages 103 to 107 (1997) discloses Cu/ZnO catalysts for the purification of feedstock for polymerizations. The performance of these catalysts at low temperatures is in need of improvement and they are sensitive to acetylene impurities.

It is an object of the present invention to remedy the abovementioned disadvantages.

We have found that this object is achieved by new and improved catalysts for the purification of ethylene comprising copper and zinc and, if desired, one or more promoters and supports and produced by precipitation, drying, calcination and pressing, with or without addition of additives, wherein the pressed catalyst particles are subjected to further calcination at from 300 to 700° C.

The catalysts of the present invention can be produced, for example, as follows:

Using conventional methods, nitrate solutions of copper and zinc can be precipitated, for example by means of sodium hydrogen carbonate solution at from 20 to 80° C., preferably from 25 to 70° C., particularly preferably from 30 to 60° C., in particular from 40 to 55° C., and these precipitates can be mixed with an $Al_2O_3$ suspension, washed, slurried and spray dried, calcined and shaped (with or without addition of additives such as graphite, talc, stearates, Walocel, starch, boron trifluoride).

The shaped catalysts obtained in this way are subjected to an after-treatment by calcination at from 300 to 700° C., preferably from 350 to 650° C., particularly preferably from 400 to 600° C., in particular from 450 to 580° C., for generally from 0.5 to 10 hours, preferably from 1 to 3 hours, particularly preferably from 1 to 2 hours, in particular from 1 to 1.5 hours. In a particularly preferred embodiment, the temperature increases during the residence time.

The novel catalysts obtained in this way generally have a BET surface area of from 10 to 100 $m^2/g$, preferably from 30 to 90 $m^2/g$, particularly preferably from 40 to 80 $m^2/g$, in particular from 50 to 75 $m^2/g$.

In the production of the catalysts of the present invention, they are generally obtained in "oxidized" form, i.e. the copper is present in the catalyst in the form of copper oxide. These catalysts of the invention can be converted into their "reduced" form by means of hydrogen, preferably in a hydrogen atmosphere at from 80 to 180° C., preferably from 100 to 160° C., particularly preferably from 120 to 140° C., and a pressure of from 1 to 50 bar, so that the copper in them is at least partly present in metallic form. In a particular embodiment, the "reduced" form of the catalysts can also be obtained in situ, i.e. by mixing sufficient amounts of hydrogen into the ethylene stream to be purified.

The composition of the catalysts in "oxidized" form can be varied within a wide range. In general, suitable catalysts comprise from 30 to 50% by weight, preferably from 35 to 45% by weight, particularly preferably from 40 to 45% by weight, of CuO, from 30 to 50% by weight, preferably from 35 to 45% by weight, particularly preferably from 40 to 45% by weight, of ZnO, from 5 to 40% by weight, preferably from 10 to 30% by weight, particularly preferably from 20 to 30% by weight, of $Al_2O_3$, $SiO_2$, $TiO_2$, MgO, iron oxides or mixtures thereof and from 0 to 5% by weight, preferably from 0 to 2% by weight, particularly preferably from 0 to 1% by weight, of promoters, and preferably consist of these except for trace components which are associated with the abovementioned components.

Suitable promoters are potassium, sodium, manganese, chromium, cobalt, tungsten, molybdenum, nickel, iron, magnesium, calcium or mixtures thereof, preferably potassium, manganese, chromium, molybdenum or mixtures thereof, particularly preferably potassium, chromium, molybdenum or mixtures thereof.

The size and shape of the catalysts of the invention can be chosen freely, for example tablets, rings, stars, wagon wheels, extrudates such as cylinders or pellets; preference is given to annular tablets or tablets.

The purification of ethylene using the catalysts of the present invention can be carried out as follows:

The ethylene to be purified can, in a two-stage process, be reacted a) in the presence of hydrogen over the catalysts of the present invention in the reduced state at from 70 to 110° C., preferably from 75 to 100° C., particularly preferably from 80 to 95° C., and a pressure of from 5 to 80 bar, preferably from 10 to 70 bar, particularly preferably from 20 to 60 bar, and subsequently b) over the catalysts of the present invention in the oxidized state at from 70 to 110° C., preferably from 75 to 100° C., particularly preferably from 80 to 95° C., and a pressure of from 5 to 80 bar, preferably from 10 to 70 bar, particularly preferably from 20 to 60 bar.

The catalysts of the present invention have a higher resistance to acetylenes than catalysts which have not undergone an after-treatment according to the invention by subsequent calcination of the shaped bodies. The catalysts of the present invention can be operated at a content of acetylenes of up to 200 ppm in the ethylene to be purified.

This two-stage process can be preceded by a hydrogenation step in which the ethylene to be purified is passed together with a sufficient amount of hydrogen over a hydrogenation catalyst, e.g. a noble metal hydrogenation catalyst, for example 0.3% by weight of Pd on an $Al_2O_3$ support. This is generally appropriate when large amounts of acetylenes, i.e. amounts of more than 200 ppm, are present in the ethylene to be purified.

EXAMPLES

Example 1

Production of the Comparative Catalyst

A mixed metal nitrate solution is prepared from 54% strength nitric acid, copper metal and zinc oxide, with the Cu/Zn ratio having to be 100:103. Using this solution, a precipitation with 20% strength sodium carbonate solution is carried out in an aluminum hydroxide slurry. The precipitate slurry produced in this way is subsequently filtered in a filter press and washed. After filtration and washing of the filtercake, the filtercake was slurried, filtered again and washed [electrical conductivity: less than 150 microsiemens; nitrate content: less than 25 ppm]. The filtercake was slurried with water to produce a 20% strength by weight suspension and this was spray dried to give a powder which was calcined for 1 hour at 525° C. in a rotary tube. [The loss on ignition determined by the measurement method GV 900 (loss on ignition at 900° C.) was 12% by weight.] The powder obtained in this way was mixed with 1% by weight of graphite and pressed to form cylindrical tablets having a diameter of 5 mm and a thickness of 3 mm. These contained 40% by weight of CuO, 40% by weight of ZnO, 19.9% by weight of $Al_2O_3$ and 0.1% by weight of $K_2O$ as promoter. The bulk density was 1.2 kg/l, the porosity was 0.3 ml/g, and the BET surface area was 125 $m^2/g$.

Example 2

Production of the Catalyst of the Present Invention

The conventional catalyst obtained as described above was calcined in a rotary tube at 490° C. in the inlet zone and 550° C. in the outlet zone, i.e. at a temperature which increased during the residence time, for 1.2 hours. The bulk density was 1.24 kg/l, the porosity was 0.34 ml/g, and the BET surface area was 64 $m^2/g$.

Example 3

Preparation of Carbon Dioxide from Carbon Monoxide

A gas mixture comprising 1125 standard l/h of nitrogen and 0.1% by volume of carbon monoxide was passed through a test apparatus comprising an adiabatically operated reactor containing a catalyst charge of 450 ml at a space velocity of 2500 standard liters of gas per liter of catalyst and hour at from 90 to 120° C. At the outlet, the remaining unreacted carbon monoxide was measured. The conversion and the temperature required are a measure of the effectiveness.

The results are reported below.

Catalyst as Described in Example 1

At a reaction temperature of 91° C., relatively no oxidation took place; all the CO broke through, i.e. it was found again at the outlet of the test apparatus. At 120° C., the conversion was greater than 99% only during the first minutes; after 15 minutes, 90 ppm of CO were present in the tailgas (conversion: 91%), while after 10 hours large amounts broke through and the content was 360 ppm (conversion: 36%).

Catalyst as Described in Example 2

At a reaction temperature of 91° C., the gas at the outlet of the test apparatus contained only 9 ppm of CO both after 10 hours and after 18 hours. The conversion was thus 99.1% after both 10 hours and 18 hours.

We claim:

1. A process for the purification of contaminated ethylene using a catalyst comprising copper and zinc and optionally one or more promoters and supports, which catalyst has been produced by precipitation, drying, calcination and shaping, with or without addition of additives, which process comprises reacting the ethylene
   a) over the catalyst in which copper is at least partly present in metallic form, in the presence of hydrogen at from 70 to 110° C. and a pressure of from 5 to 80 bar, and subsequently
   b) over the catalyst in which copper is present in the form of copper oxide at from 70 to 110° C. and a pressure of from 5 to 80 bar,
   and wherein the catalyst used for the process has been subjected, after shaping, to a further calcination at from 300 to 700° C.

2. A process as claimed in claim 1, wherein the catalyst consists of copper and zinc, optionally partly in oxidic form.

3. A process as claimed in claim 1, wherein the catalyst has a BET surface area of from 10 to 100 $m^2/g$.

4. A process as claimed in claim 1, wherein the contaminated ethylene comprises catalyst poisons which adversely affect the performance of organoaluminum Ziegler-Natta catalysts or chromium-containing Phillips catalysts.

5. A process as claimed in claim 1, wherein the contaminated ethylene comprises acetylene impurities and/or CO.

6. A process for the purification of contaminated ethylene in the presence of a catalyst, which comprises reacting the contaminated ethylene at from 70 to 110° C. and a pressure of from 5 to 80 bar
   a) with the catalyst in a reduced state in the presence of hydrogen, and subsequently
   b) with the catalyst in an oxidized state;
   wherein the catalyst comprises copper and zinc and optionally one or more promoters and supports, said copper being present in the oxidized form of the catalyst in form of copper oxide and being present in the reduced state of the catalyst at least partly sin metallic form; and
   wherein the catalyst is obtained by a procedure comprising the steps of precipitation, drying, a first calcination prior to shaping, then shaping, with or without addition of additives, to form shaped catalyst particles, and a second calcination of shaped catalyst particles at from 300 to 700° C.

7. A process as claimed in claim 6, wherein the catalyst consists of copper and zinc, optionally partly, in oxidic form.

8. A process as claimed in claim 6, wherein the catalyst has a BET surface area of from 10 to 100 $m^2/g$.

9. A process as claimed in claim 6, wherein the contaminated ethylene comprises catalyst poisons which adversely affect the performance of organoaluminum Ziegler-Natta catalysts or chromium-containing Phillips catalysts.

10. A process as claimed in claim 6, wherein the contaminated ethylene comprises acetylene impurities and/or CO.

* * * * *

UNITED STATES PATENT AND TRADEMARK OFFICE
CERTIFICATE OF CORRECTION

| | | |
|---|---|---|
| PATENT NO. | : 7,314,965 B2 | Page 1 of 1 |
| APPLICATION NO. | : 10/477356 | |
| DATED | : January 1, 2008 | |
| INVENTOR(S) | : Vorberg et al. | |

It is certified that error appears in the above-identified patent and that said Letters Patent is hereby corrected as shown below:

In Claim 6, col. 4, indicated line 41:

"partly sin" should read --partly in--

Signed and Sealed this

Twentieth Day of May, 2008

JON W. DUDAS
*Director of the United States Patent and Trademark Office*